US012625283B2

(12) United States Patent
Polijanczuk et al.

(10) Patent No.: US 12,625,283 B2
(45) Date of Patent: May 12, 2026

(54) DUAL GAMMA RAY AND VISIBLE LIGHT IMAGING DEVICE

(71) Applicant: SERAC IMAGING SYSTEMS LTD, London (GB)

(72) Inventors: Andrew Victor Polijanczuk, London (GB); George William Wylde, London (GB); Matthew Robert Hickey, London (GB); Paul Andrew Cload, London (GB); Mark Joseph Rosser, London (GB)

(73) Assignee: SERAC IMAGING SYSTEMS LTD, London (GB)

( * ) Notice: Subject to any disclaimer, the term of this patent is extended or adjusted under 35 U.S.C. 154(b) by 78 days.

(21) Appl. No.: 18/274,935

(22) PCT Filed: Jan. 28, 2022

(86) PCT No.: PCT/GB2022/050240
§ 371 (c)(1),
(2) Date: Jul. 28, 2023

(87) PCT Pub. No.: WO2022/162387
PCT Pub. Date: Aug. 4, 2022

(65) Prior Publication Data
US 2024/0111064 A1 Apr. 4, 2024

(30) Foreign Application Priority Data
Jan. 29, 2021 (GB) ...................................... 2101278

(51) Int. Cl.
*G01T 1/20* (2006.01)
*A61B 6/00* (2024.01)
(Continued)

(52) U.S. Cl.
CPC ........ *G01T 1/20185* (2020.05); *A61B 6/4258* (2013.01); *A61B 6/4417* (2013.01); *G21F 1/00* (2013.01); *A61B 6/508* (2013.01)

(58) Field of Classification Search
CPC ..... A61B 6/4258; A61B 6/4417; A61B 6/508; G01T 1/20185; G21F 1/00
See application file for complete search history.

(56) References Cited

U.S. PATENT DOCUMENTS 4,076,984 A * 2/1978 Gromov ............... G03B 42/028
378/98.3
4,521,688 A 6/1985 Yin
(Continued)

FOREIGN PATENT DOCUMENTS

CA 2254877 A1 11/1997
CN 207663074 U 7/2018
(Continued)

OTHER PUBLICATIONS

International Search Report for PCT/GB2022/050240 mailed on Jun. 28, 2022.
(Continued)

*Primary Examiner* — Blake C Riddick
(74) *Attorney, Agent, or Firm* — Bookoff McAndrews, PLLC

(57) ABSTRACT

A medical imaging device for use in imaging a subject using both gamma rays and light rays emanating from the subject, the device comprising: separation means to separate gamma rays and light rays emanating from the subject into a gamma ray channel comprising gamma rays and a light ray channel comprising light rays; first sensor means arranged to receive and detect gamma rays from the gamma ray channel and to generate first signals for use in forming a first image of the subject; second sensor means arranged to receive and detect light rays from the light ray channel and to generate second
(Continued)

signals for use in forming a second image of the subject; wherein the first sensor means and the second sensor means are arranged to receive gamma rays and light rays, respectively, which propagate from the subject upon substantially coincident paths.

19 Claims, 7 Drawing Sheets

(51) Int. Cl.

| | |
|---|---|
| *A61B 6/42* | (2024.01) |
| *A61B 6/50* | (2024.01) |
| *G21F 1/00* | (2006.01) |

(56) References Cited

U.S. PATENT DOCUMENTS

| | | | | |
|---|---|---|---|---|
| 4,791,300 | A | 12/1988 | Yin | |
| 5,204,533 | A * | 4/1993 | Simonet | G01T 7/00 |
| | | | | 250/361 R |
| 5,371,370 | A * | 12/1994 | Lightfoot | G01T 1/2019 |
| | | | | 250/252.1 |
| 5,557,107 | A * | 9/1996 | Carcreff | G01T 7/00 |
| | | | | 250/361 R |
| 5,596,198 | A * | 1/1997 | Perez-Mendez | G01T 1/1642 |
| | | | | 250/366 |
| 5,864,146 | A * | 1/1999 | Karellas | A61B 6/502 |
| | | | | 378/191 |
| 6,271,510 | B1 * | 8/2001 | Boxen | G01T 1/201 |
| | | | | 250/227.2 |
| 6,782,123 | B1 * | 8/2004 | Guillon | G01C 11/06 |
| | | | | 348/42 |
| 7,173,251 | B2 | 2/2007 | Fraser et al. | |
| 2002/0070365 | A1 * | 6/2002 | Karellas | A61B 6/4241 |
| | | | | 250/581 |
| 2004/0021766 | A1 * | 2/2004 | Daniilidis | H04N 23/11 |
| | | | | 348/36 |
| 2005/0023479 | A1 * | 2/2005 | Grodzins | G01T 3/06 |
| | | | | 250/390.11 |
| 2007/0267577 | A1 | 11/2007 | Kindem | |
| 2008/0128625 | A1 * | 6/2008 | Lamadie | G01T 1/295 |
| | | | | 250/361 R |
| 2008/0242980 | A1 * | 10/2008 | Lees | A61B 6/4258 |
| | | | | 250/363.04 |
| 2010/0301221 | A1 * | 12/2010 | Nakamura | G01T 1/1642 |
| | | | | 250/366 |
| 2011/0114844 | A1 * | 5/2011 | Idoine | G01T 1/1648 |
| | | | | 250/363.1 |
| 2014/0175296 | A1 * | 6/2014 | Benlloch Baviera | |
| | | | | G01T 1/2002 |
| | | | | 250/366 |
| 2014/0231661 | A1 * | 8/2014 | Baroni | G01T 3/065 |
| | | | | 250/390.07 |
| 2016/0245930 | A1 * | 8/2016 | van Arendonk | G01T 1/2006 |
| 2017/0010367 | A1 | 1/2017 | Dejavdan | |
| 2018/0228424 | A1 * | 8/2018 | Hong | A61B 5/418 |
| 2020/0166655 | A1 * | 5/2020 | Pozzi | G01T 1/20 |
| 2022/0011451 | A1 * | 1/2022 | Ilisie | G01T 1/249 |
| 2023/0075571 | A1 * | 3/2023 | Lecoq | G01T 1/2008 |
| 2023/0266257 | A1 * | 8/2023 | Wooldridge | G01N 23/222 |
| | | | | 250/390.04 |

FOREIGN PATENT DOCUMENTS

| | | | |
|---|---|---|---|
| CN | 106104305 B | | 6/2020 |
| JP | H11505142 A | | 5/1999 |
| JP | 2012504749 A | | 2/2012 |
| JP | 2013-127380 A | | 6/2013 |
| JP | 2014-98605 A | | 5/2014 |
| JP | 2014098605 A | * | 5/2014 |
| JP | 2016223997 A | | 12/2016 |
| JP | 2021500550 A | | 1/2021 |

OTHER PUBLICATIONS

United Kingdom Search Report for Priority Application No. 2101278. 6, dated Nov. 1, 2021.

Written Opinion of the International Searching Authority for PCT/GB2022/050240 mailed on Jun. 28, 2022.

Lees, J.E. et al., "A Multimodality Hybrid Gamma-Optical Camera for Intraoperative Imaging", Sensors, 2017, vol. 17, Issue No. 3, Article No. 554, pp. 1-12.

Bugby, S.L. et al., "Characterisation of a high resolution small field of view portable gamma camera", Physica Medica, 2014, vol. 30, Issue No. 3, pp. 331-339.

* cited by examiner

10

11

20

21

DUAL GAMMA RAY AND VISIBLE LIGHT IMAGING DEVICE

FIELD OF THE INVENTION

This invention relates to an imaging device. In particular, though not exclusively, the invention relates to a medical imaging device using both gamma rays and light rays emanating from the subject, as well as methods of using the same.

BACKGROUND OF THE INVENTION

A gamma camera (also called γ-camera or scintillation camera), is a device used in medical imaging to image gamma radiation being emitted from radioisotopes. As such, the device must be suitable for the levels of gamma radiation given off by radio isotopes administered to a subject, while providing suitable resolution to allow a medical practitioner to perform medical treatment, analysis or diagnosis etc. Therefore, gamma medical imaging devices have a sensitivity and resolution that are tailored to their role. Typically the device is required to form medical images of radioisotopes with a gamma emission energy between about 35 keV and about 511 keV administered to a subject at levels between about 10 MBq and 1000 MBq for a 70 kg body weight. The dose may be adjusted to take account of the size of the subject.

Gamma cameras are commonly used to create two dimensional images in a technique known as scintigraphy. In scintigraphy radioisotopes are commonly attached to tracer agents or drugs (radiopharmaceuticals) which travel to specific organs or tissues, and in that way those target tissues can be imaged. So, this technique can create visual representations of the interior of the target for clinical analysis and medical intervention, as well as visual representation of the function of organs or tissues. Therefore, this technique goes beyond revealing internal structures hidden by the exterior of the subject, it can target certain organs or diseased states and/or provide more information about their anatomy and function.

Many gamma cameras are large, expensive and fixed, and so are typically housed in a bespoke room in a hospital. Patients are typically required to go to the location and are inserted into the body of the device to be scanned. Smaller gamma cameras with a more limited field of view are more portable but remain relatively large and unwieldy, and further maybe lacking in sensitivity and/or resolution and/or suitable field of view. Some portable cameras are known to be quite inefficient and their power use may result in overheating, which can limit the camera's usefulness in the field.

Examples of gamma cameras used in scintigraphy include in Siemens Healthineers' Symbia Intevo Excel, Oncovision's Sentinella and Digirad's Ergo™ Imaging System.

In addition, attempts have been made to align the gamma ray images with normal visible (optical) images of the subject. In that way the source of the gamma radiation within the body of the subject can be correlated with an external surface of the subject. This is typically done by using a gamma camera and a visible camera to image the subject at the same time. However, there is difficulty obtaining good alignment of the gamma and optical ray images due to the phenomena of parallax (schematic representation shown in FIG. 1), i.e. a displacement in the apparent position of an object viewed along two different lines of sight by the optical camera and the gamma camera.

See also U.S. Pat. No. 7,173,251, US 2008/024290 and Physica Medica 30 (2014) 331 to 339, Bugby et al. While this discloses a portable device, this device suffers from a number of limitations and drawbacks. It requires the manual adjustment and calibration of the gamma and optical field of view during construction of each unit, a time consuming process. The scintillator and substrate is manually mounted on the EMCCD sensor and secured with tape. The EMCCD detector requires active cooling and must be kept at below 0° C. during operation, to minimise electronic noise that degrades image quality. Heat removed from the EMCCD is absorbed by a phase change material that has a finite capacity to keep the sensor at the desired temperature. As such, maintaining the sensor at the required temperature during continuous operation is not possible. Moreover, the sensor must be kept in a high vacuum chamber to avoid condensation on the sensor when at these low temperatures. Again this is difficult, and takes some hours of time during assembly and requires a design capable of maintaining high vacuum for years of product life time. This design contains a separate electronics box for control and data processing prior to transfer to a computer for offline image reconstruction and display, which is slow and not convenient. The device requires multiple cables to supply power and transfer data signals from the gamma and optical sensors with separate communication channels (cables) for the gamma and optical images.

There remains a need in the art for improved solutions to the problem of gamma ray imaging.

SUMMARY OF THE INVENTION

Herein disclosed, is a device for use in imaging a subject using both gamma rays and light rays emanating from the subject, the device comprising:

separation means to separate gamma rays and light rays emanating from the subject into a gamma ray channel comprising gamma rays and a light ray channel comprising light rays;

first sensor means arranged to receive and detect gamma rays from the gamma ray channel and to generate first signals for use in forming a first image of the subject;

second sensor means arranged to receive and detect light rays from the light ray channel and to generate second signals for use in forming a second image of the subject;

wherein the first sensor means and the second sensor means are arranged to receive gamma rays and light rays, respectively, which propagate from the subject upon substantially coincident paths.

In a first aspect of the invention, there is provided a medical imaging device for use in imaging a subject using both gamma rays and light rays emanating from the subject, the device comprising:

separation means to separate gamma rays and light rays emanating from the subject into a gamma ray channel comprising gamma rays and a light ray channel comprising light rays;

first sensor means arranged to receive and detect gamma rays from the gamma ray channel and to generate first signals for use in forming a first image of the subject;

second sensor means arranged to receive and detect light rays from the light ray channel and to generate second signals for use in forming a second image of the subject;

wherein the first sensor means and the second sensor means are arranged to receive gamma rays and light rays, respectively, which propagate from the subject upon substantially coincident paths.

As explained further herein below, the present invention provides a dual gamma and optical ray imaging device which is substantially free from the problems of parallax and which has excellent resolution and sensitivity. The invention also provides for a compact design that is light and portable and so may be taken directly to patients. The present invention is also relatively simple to manufacture reproducibly. The present invention also provides for prolonged use due to low power usage and efficient integrated heat removal structures. Furthermore, the present invention includes a variable pinhole collimator allowing the operator to conveniently select a pinhole of the preferred dimensions for the particular application at hand without need to disassemble the device, reassemble with an alternative collimator, or realign/recalibrate. In an embodiment the variable pinhole collimator comprises a cassette wheel, rotatable to bring one of the one or more pinholes into alignment with the gamma ray channel. The cassette wheel may contain holes of different diameters or geometries In a further embodiment, the holes may be spaced evenly apart and spaced in from the circumference of the wheel. Also, advantageously, the selectable pinholes can be used to change the resolution/sensitivity of the camera as required by the application (e.g., a larger pinhole to find the source of the radiation or for rapid imaging, and a smaller pinhole for higher resolution imaging).

Gamma ray medical imaging devices are not suitable for imaging all forms of electromagnetic radiation such as infrared, ultraviolet and X-ray radiation types. In particular, although both gamma and x-ray radiation are types of ionising radiation it should be understood that gamma rays are distinguished from X-rays in that gamma rays, like alpha and beta particles, originate from the radioactive decay of an unstable nucleus, whereas X-rays originate from electrons outside the nucleus.

So, sources of gamma rays originate from radioactive materials that decay over time. X-rays on the other hand are actively produced by X-ray tubes, in which electrons are accelerated in a vacuum and impacted on a metal plate. Gamma rays generally have higher energies than X-rays. X-rays typically have energies in the range 100 eV to 100,000 eV (or 100 keV) whereas gamma rays generally have energies greater than about 100 keV. Furthermore, X-ray imaging is typically completed rapidly with image acquisition completed within seconds or, at most, 1 to 2 minutes. Scintigraphic images of gamma emitting radio isotopes typically take from about 5 to 40 minutes to acquire, presenting additional challenges in terms of imaging device design. This means that in practical terms devices tailored to gamma ray detection are not suitable for X-ray imaging, and vice versa. This is because X-ray detection/imaging systems have low efficiency for gamma ray detection, as the higher energy gamma rays tend to pass through the system without being detected. Conversely, detection/imaging systems used for gamma ray imaging are substantively unresponsive to the lower energy X-rays. In an embodiment the device is optimised for gamma ray detection. In an embodiment the device is not used to detect X-rays. In an embodiment the device detects ionising radiation with energies greater than about 30 keV. In an embodiment the device detects ionising radiation with energies greater than about 100 keV. In an embodiment the device is adapted to detect gamma rays emitted from a radio isotope source. In an embodiment the device is adapted to detect gamma rays emitted from a radio isotope source administered to a subject.

In an embodiment the light rays in the light ray channel are in the visible, UV or IR regions, optionally the light rays are caused by fluorescence, and further optionally by UV, visible or near infra-red fluorescence. The visible light source may take any reasonable form, and is selected to suit the application the device is being used for. For example, if the subject contains a UV fluorescent substance, then UV light may be applied to the subject to cause this substance to fluoresce. The device may be equipped with an integrated light source to illuminate the subject at the appropriate frequency. Typically, the object is illuminated with visible light which is detectable to the human eye.

In an embodiment the device does not comprise a separation means to separate gamma rays and light rays emanating from the subject into a gamma ray channel comprising gamma rays and a light ray channel comprising light rays. In an embodiment the device does not use light rays and does not generate second signals for use in forming a second image of the subject.

Herein disclosed, the device according to the aspects of the invention which does not comprise a separation means to separate gamma rays and light rays emanating from the subject into a gamma ray channel comprising gamma rays and a light ray channel comprising light rays; and does not comprise a second sensor means arranged to receive and detect light rays from the light ray channel and to generate second signals for use in forming a second image of the subject.

Herein disclosed is a device for use in imaging a subject using gamma rays emanating from the subject, the device comprising:

channeling means to form a gamma ray channel, the gamma ray channel comprising gamma rays emanating from the subject;

first sensor means arranged to receive and detect gamma rays from the gamma ray channel and to generate first signals for use in forming a first image of the subject; and wherein the first sensor means comprises a gamma ray scintillator means responsive to gamma rays and which produces scintillator output flashes of light in response to incidences of gamma rays, and wherein the gamma ray scintillator is deposited on the surface of a Fibre Optic Plate (FOP), optionally a tapered Fibre Optic Plate (tFOP).

Herein disclosed, the channeling means is arranged to allow a beam or column of gamma rays emanating from the subject to propagate to a gamma ray detection means, wherein the beam or column of gamma rays is suitable for detection by a gamma ray detection means (e.g. such a means comprising a gamma ray scintillator and/or a CMOS detector). For example, a channeling means may comprise a window or pinhole in a gamma ray shielded chamber. In some applications, the generation of a visible light image in addition to the gamma ray image is not necessary. Advantageously, when the gamma ray scintillator is deposited on the surface of the Fibre Optic Plate (FOP) or tapered Fibre Optic Plate (tFOP), the interface between the two layers is substantially eliminated; as such the loss of signal and/or resolution associated with such interfaces are likewise substantially mitigated/eliminated.

In an embodiment the separation means is arranged to propagate the light ray channel substantially orthogonally to the gamma ray channel. In an embodiment the separation means comprises a reflective or refractive material. In an embodiment the separation means comprises one or more of a mirror, prism, or lens. In an embodiment the separation means comprises a reflective surface that reflects light rays incident upon the reflective surface. In an embodiment the separation means does not comprise a lens prior to the reflective surface. In an embodiment the separation means is arranged before the scintillator, relative to the gamma and light rays propagating from the subject. In an embodiment a separation means is not arranged after the scintillator, relative to the gamma and light rays propagating from the subject. In an embodiment the separation means is substantially transparent to gamma rays. In an embodiment the gamma rays are not substantially attenuated by the separation means. In an embodiment the separation means comprises a mirror arranged at substantially 45 degrees to gamma and light rays propagating from the subject. In an embodiment the mirror is between 0.01 and 3 mm thick, optionally, between 0.1 and 2 mm thick, further optionally between 0.5 and 1.5 mm thick in order to provide sufficient mechanical robustness for day to day use of the device while minimising the affect on the gamma rays. It should be noted that the mirror, lens, optical component, or the like in the path of the gamma ray channel will absorb/attenuate/scatter some of the gamma rays, and so effect the sensitivity of the device. For example, a 3 mm thick mirror may absorb/scatter/attenuate in excess of 10% of the gamma ray photons at 150 keV, whereas a 0.5 mm thick mirror would absorb about 2%. This is particularly important in the case of medical imaging where the gamma ray source may be inside a patient, and so the amount of radioisotope administered is as low as possible for safety reasons and high sensitivity to relatively low levels of gamma radiation is therefore important.

The separation means is arranged to separate the gamma rays and visible light rays into two separate channels. High energy gamma rays pass through the separation means, whereas, the visible light is directed in a different direction. In that way gamma and light rays propagating from the subject upon substantially coincident paths are separated, and can be processed separately. For example when the separation means is a mirror, the light rays will be reflected by the mirror whereas the higher energy gamma rays will pass through it. The appropriate sensors can be arranged to receive the gamma and light ray channels respectively.

In an embodiment the distance gamma rays travel from the separation means to the first sensor means is substantially the same distance as the distance light rays travel from the separation means to the second sensor means. In an embodiment the field of view (FOV) of the first sensor means and second sensor means are substantially fully aligned. In an embodiment the distance gamma rays travel from the separation means to the pinhole is substantially the same distance as the distance light rays travel from the separation means to the second sensor means (e.g. to a lens in the second sensor). In an embodiment the field of view (FOV) of the first sensor means and second sensor means are substantially fully aligned. In an embodiment the distance gamma rays travel from the separation means to the pinhole is 0.1 to 100 mm, optionally 0.5 to 20 mm, further optionally 5 to 15 mm, and still further optionally 10-12 mm. In an embodiment the distance light rays travel from the separation means to the second sensor means is 0.1 to 100 mm, optionally 0.5 to 20 mm, and further optionally 5 to 15 mm. The distance may be determined as the path between the first sensor means and the separation means and wherein the path passes through the pinhole and meets the sensor at an angle of 90°. Advantageously, there is therefore no need for adjustment or calibration of the alignment of the FOVs during build or adjustment/recalibration after shipping or movement.

In an embodiment the distance gamma rays travel from the separation means to the first sensor means is 5 to 100 mm, optionally 10 to 60 mm, and further optionally 20 to 40 mm. In an embodiment the distance light rays travel from the separation means to the second sensor means is 5 to 100 mm, optionally 10 to 60 mm, and further optionally 20 to 40 mm. In an embodiment the distance gamma rays travel from the separation means to the scintillator detection plane is 5 to 100 mm, optionally 10 to 60 mm, and further optionally 20 to 40 mm. The distance may be determined as the shortest path between the sensor and separation means and wherein the path passes through the pinhole, e.g. the path connects/contacts the facing surfaces of the sensor and separation means and follows the direction of the gamma ray channel through the pinhole. Advantageously, there is therefore no need for adjustment or calibration of the alignment of the FOVs during build or adjustment/recalibration after shipping or movement.

Advantageously, the problem of parallax is substantially avoided/mitigated by the arrangement of the invention. Devices of the prior art typically use two spaced apart cameras (one optical and one gamma), and this spacing apart can lead to an apparent visible displacement of the position of an object viewed along those two different lines of sight. This problem is highlighted schematically in FIG. 1. By contrast, advantageously, the device of the invention splits the rays being emitted by the subject into a visible and gamma ray channel, and because the first sensor means and second sensor means are very close together, the device can be configured by design such that the gamma and optical images have essentially the same diameter field of view and the centre points of the fields of view are essentially coincident and remain coincident irrespective of the distance from the subject. Advantageously, by being close together and the same distance from the subject means the images are aligned; so they are the same size and have the same centre point. Therefore, for example, a surgeon using the invention to aid in the removal of a tumour from a subject (where the cancer cells of the tumour have been tagged with a radio isotope) can have confidence that the superimposition of the visible and gamma images do not suffer from misalignment. This means the tumour can be targeted more specifically and can be removed with more confidence, and less healthy tissue may be sacrificed to allow for any error associated with parallax.

In an embodiment the second sensor means comprises a camera to detect light rays. In an embodiment the camera has a detection area to detect light rays of 10 to 100 mm², optionally 20 to 60 mm², and further optionally 35 to 45 mm². In an embodiment the camera is substantially planer. In an embodiment the camera is mounted on a circuit board. In an embodiment the camera is a digital camera. In an embodiment the camera is suitable for use in a mobile (cell) phone or tablet. In an embodiment the camera comprises a global shutter or a rolling shutter. Preferentially a global shutter facilitates real-time display of video images.

In an embodiment the second sensor means comprises second signal digitisation means to convert light rays detected by the second sensor means into second signals for use in forming a second image of the subject. Advantageously, it is useful to digitise the detected visible light. This allows for storage, manipulation and transmission of the image data as needed.

The digitised signals of the first and/or second sensor means can be processed on-board the device or they can be transmitted to a further device for processing or further processing. For example, filters and data conditioning processes can be applied to the data as necessary to improve the final image produced. As such, pre-processing using firmware within the device provides for real-time streaming of both optical video and gamma images using a single data connection, and the low power consumption requirements enable this single cable to also function as the power supply. So, beneficially, a single cable connection can provide both power and communication needs. The on-board signal processing prior to transmission of the gamma and optical data streams may also provide for efficient wireless transmission of the data. Advantageously, the on-board signal processing enables two signal channels (i.e. gamma and optical) to be streamed simultaneously in real-time.

In an embodiment the first sensor means is housed in a chamber substantially opaque to gamma rays, the chamber comprising a window arranged to receive gamma rays from the gamma ray channel, and wherein the window is substantially transparent to gamma rays. Advantageously, the chamber is arranged to allow gamma rays from the gamma ray channel to be detected by the first sensor means, and to substantially block out other sources of gamma rays.

In an embodiment the separation means separates the gamma rays and light rays at a position close to the window. Close proximity of the separation means to the window maximises the sensitivity of the device while facilitating a small form factor. In an embodiment the separation means separates the light rays at a distance of between 1 and 50 mm from the window, optionally between 5 and 30 mm from the window, and further optionally between 10 and 20 mm from the window. In an embodiment the centre of the field of view of the second sensor means is in line with the centre of the window. Advantageously, as previously mentioned, having the first sensor means and second sensor means as close as possible means that aligning the FOVs of the gamma and optical images is achieved by design, and the device can also be made very compact.

In an embodiment the chamber comprises a tapered end, the tapered end tapering towards the window. In an embodiment the chamber comprises a substantially cone-shaped end, the cone narrowing towards the window. In an embodiment the chamber comprises a recessed area proximate to the window. In an embodiment the taper, cone-shaped end, and/or recessed area is arranged to accommodate, or partially accommodate, the second sensor. In an embodiment the taper, cone-shaped end, and/or recessed area is arranged to accommodate the second sensor means such that the second sensor means is in close proximity to the window. It is advantageous for the first and second sensor means to be in close proximity to each other, for example allowing for good alignment of their field of views and aiding in producing an overall compact design. However, as the chamber approaches the separation means, the chamber can in effect crowd out the space needed for the second sensor means. Advantageously, by tapering the chamber towards the window, space is in effect created near to and adjacent to the separation means, and so this provides room to bring the second sensor means much closer to the separation means and to bring the separation means close to the window. Therefore, by tapering the chamber, both the first and second sensor means can be brought as close as possible to the separation means, so providing better alignment of their respective field of views and greatly reducing the overall volume necessary to house the device. While a tapered cone chamber is a convenient way to obtain the benefits outlined above, this could also be accomplished in other ways, for example by making a depression or recessed area in the chamber to allow for the second sensor means to get close to the window. The size and/or weight and/or cost of the device may also be reduced by using less material for the chamber.

In an embodiment the chamber is arranged to substantially exclude background gamma radiation. In an embodiment the chamber is arranged to attenuate more than 90% of incoming gamma rays at 150 keV. In an embodiment the chamber is arranged to attenuate more than 95% of incoming gamma rays at 150 keV. In an embodiment the chamber is arranged to attenuate more than 98% of incoming gamma rays at 150 keV. In an embodiment the chamber is arranged to exclude more than 99% of background gamma radiation. In an embodiment the chamber is arranged to attenuate more than 99.99% of incoming gamma rays at 150 keV. In an embodiment the chamber comprises a material with a density of greater than 11 $g/cm^3$, and optionally greater than 19 $g/cm^3$.

In an embodiment the device or chamber comprises a thermal dissipation means to remove heat from the device. In an embodiment the device or chamber comprises, or is comprised of, a material which is thermally conductive. In an embodiment the device or chamber comprises, or is comprised of, a material which has a thermal conductivity of between 10 to 500 W/mK, optionally 50 to 300 W/mK, and further optionally 100 to 200 W/mK. In an embodiment the device or chamber comprises a heat sink, or is thermally connected to an external heat dissipation means or heat sink. In this way the passive cooling means reduces the electrical power requirements and facilitates a single cable, power-over-internet (POE), connectivity. Fewer cables also facilitate use and a smaller more portable device. In an embodiment the device or chamber comprises a low power Peltier, heat exchange pipes, and/or a cooling fan. In an embodiment the device or chamber comprises a low power Peltier. In an embodiment the device or chamber does not comprise a fan. In an embodiment the device or chamber is connected to a low power Peltier, heat exchange pipes, and/or a cooling fan. In an embodiment the low power Peltier has a pump power of between 0.1 and 20 W, optionally between 0.5 and 10 W, and further optionally between 4 and 6 W. In an embodiment the device or chamber comprises lead or tungsten. In an embodiment the chamber comprises, or is comprised of, lead or tungsten. In an embodiment the chamber consists of tungsten. In an embodiment the lead or tungsten is arranged to provide gamma ray shielding to the chamber and to conduct heat away from the chamber. For example, the tungsten shielding may be used to prevent heat moving into the core, and/or by dissipating/transferring any heat to the external environment. In an embodiment the device does not comprise a phase changing material used to provide cooling. The build-up of heat in the device can adversely affect the performance of components like the sensors or image intensifiers and so can limit the use of the device. For example, electrical signal noise increases as a function of temperature and so this can degrade image quality. The noise decreases again as the temperature drops. In prior art devices such as in the Physica Medica publication mentioned herein above, it was found that the device could not be operated continuously for long periods and required long rest periods to allow the device to cool. Excess heat may even damage the device. Removing heat from the device in a simple and convenient way without increasing the bulk/complexity of the device would be beneficial. Advantageously, in an embodiment, the use of the tungsten of the chamber to perform the dual function of both preventing unwanted gamma rays from reaching the first sensor means and as a useful and convenient way of dissipating heat from the device to the external environment by thermal conduction provides stable performance in continuous operation at a wide range of operating temperatures. One benefit of the device, in an embodiment of the present invention, is its small form factor and light weight, so avoiding a heat sink of finite capacity, fans, cooling pipes, cooling fluids, and the like is also advantageous. Dissipation of excess heat through the thermal conduction is advantageously convenient for an ergonomic design with that can be easily cleaned as there is no need for vents or grills to permit air cooling, for example. Advantageously, by avoiding the need for fans/fins or holes in the case etc., hygienic maintenance of the device is simplified and so made easier in a busy hospital environment.

In an embodiment the chamber comprises one or more communication lines, or ports arranged to receive communication lines. The chamber can be arranged to allow necessary communication lines while still acting to shield the first sensor means from unwanted gamma rays.

The window, which allows gamma rays into the chamber, can take many forms. Typically it will take the form of a 'pinhole'. The size of the pinhole may be chosen to suit need, e.g. balancing resolution and sensitivity. In an embodiment the window is an aperture. In an embodiment the window comprises a region which is not transparent to light rays but is transparent to gamma rays. In an embodiment the window is substantially round. In an embodiment the dimensions of the window are in the range 0.1 to 10 mm, optionally 0.5 to 7.5 mm, and further optionally 1 to 5 mm in diameter. In an embodiment the size of the window is fixed. In an embodiment the size of the window(s) can be selected according to need e.g. a cassette wheel. In an embodiment the dimensions of the window are selected from any one of 1, 2, 3 or 5 mm e.g. for imaging a person. An alternative set of pinholes can be provided so that a cassette wheel is configured with the optimum range of sizes for applications where the best compromise of sensitivity, resolution and image acquisition times may be different. The device is therefore advantageously easily modified for various applications. e.g. for small animal imaging high resolution may be required, but a longer acquisition might be acceptable and so smaller pinholes could be preferred; where a very large field of view is of interest e.g. inanimate objects, high resolution is less important and larger pinholes could be preferred. Where levels of radioactivity are to be imaged are high, smaller pinholes might still be acceptable so that resolution need not be sacrificed in favour of faster imaging and may be advantageous in mitigating potential detector saturation in situations where high levels of gamma radiation are imaged.

The window may also take other forms. In an embodiment the size and/or location of the window may be varied (e.g. using an iris). In an embodiment the chamber comprises two or more windows arranged to receive gamma rays emanating from the subject. In an embodiment the device is arranged to deconvolute the signals obtained from one or more windows. In an embodiment the window is a coded aperture. In an embodiment the device is arranged to deconvolute the signals obtained from a coded aperture. In optics and imaging, the term deconvolution is used to refer to the process of reversing optical distortions that can take place using an optical/imaging instrument. Deconvolution is usually done by the skilled person in the digital domain by using one or more algorithms. As such, deconvolution can be used to enhance signals, or restore original signals, from the recorded data. Advantageously, deconvolution produces clearer resultant images.

In an embodiment the window comprises any one of a pinhole, two or more pinholes, collimator, iris, shutter, and coded aperture. In an embodiment the window comprises, or is comprised of, a pinhole. In an embodiment the window is chamfered. Advantageously, the chamfer is formed to create the cone angle defined by the desired angular field of view of the system and provides the most efficient design in terms of achieving the required level of shielding in the smallest space. In an embodiment the window does not comprise a coded aperture. In an embodiment the window is not a titanium window. In an embodiment the window does not comprise a titanium coded aperture.

The window/pinhole can be arranged/varied to suit need. In an embodiment the angular field of view of the window is fixed and is substantially the same as the angular field of view of the second sensor means. In an embodiment the window is a pinhole and this is arranged to provide a fixed angular, variable diameter field of view. In an embodiment the angular field of view of the window is 30 to 130°, optionally 45 to 75°, and further optionally 60°. In an embodiment the pinhole is sized/dimensioned to provide an optimal balance between gamma image resolution and sensitivity. In an embodiment the pinhole is sized/dimensioned to reduce optical artefacts resulting from the gamma rays passing through the pinhole. In an embodiment the pinhole is in close proximity to the separation means.

The device can be configured and optimised for one particular use. In this way a fixed window/pinhole can be used. Alternatively, the device may be equipped with ways to vary the nature of the window, such that one window/pinhole can be swapped for another depending on the use. In an embodiment the chamber comprises a movable member comprising two or more movable windows of different sizes and/or shapes, wherein the movable member is reversibly movable such that at least one of the movable windows of different size and/or shape is arranged to form the window in the chamber. In an embodiment the movable member is a reversibly rotatable or slideable plate. In an embodiment the plate has a substantially circular cross-section. In an embodiment the movable member comprises, or consists of, tungsten or lead. In an embodiment positioning of the movable windows is controlled to maintain alignment of the gamma and optical fields of view. In an embodiment positioning of the movable windows is controlled to maintain alignment of the gamma and optical fields of view by a reversible locking mechanism. In an embodiment the movable member is driven manually or by an electric motor. In an embodiment the movable member is driven by an actuator. Advantageously, by simple means like an actuator, the nature of the window can be changed by the user without the need to open the device.

In an embodiment the first sensor means comprises a gamma ray scintillator means responsive to gamma rays and which produces scintillator output flashes of light in response to incidences of gamma rays. In this way, the high energy gamma rays are absorbed and converted into photons. It should be noted, the image intensifier is not producing electrons directly from gamma rays (i.e. by a photoelectric effect, e.g. by means of a photocathode exposed to an intense gamma ray source, which is unsuited to medical imaging). In an embodiment the gamma ray scintillator is arranged to receive the gamma rays emanating from the subject in the gamma ray channel. In an embodiment a photocathode of the image intensifier is not arranged to receive the gamma rays emanating from the subject in the gamma ray channel. In an embodiment gamma ray photons that pass through the gamma ray scintillator are substantially absorbed by the tFOP and do not reach the image intensifier. In an embodiment the first sensor means does not comprise a photocathode prior to a gamma ray scintillator means.

In an embodiment the gamma ray scintillator means is arranged to provide for a fixed angular field of view. In an embodiment the window and the gamma ray scintillator means are arranged together to provide a fixed angular field of view. Advantageously, by optimising the size and shape of the window/pinhole and the distance the scintillator means is away from the window, the full surface area of the scintillator can be optimally used.

In an embodiment the gamma ray scintillator is deposited on the surface of a Fibre Optic Plate (FOP). Advantageously, by doing this any interface between the two layers is mitigated or substantially eliminated. In an embodiment the gamma ray scintillator is deposited on the surface of a tapered Fibre Optic Plate (tFOP).

In an embodiment the gamma ray scintillator means is responsive to gamma rays having an energy value in the range 35 to 750 KeV. In an embodiment the gamma ray scintillator is a semiconductor such as CdTe or CdZnTe. In an embodiment the gamma ray scintillator means an inorganic metal halide crystal or a metal halide crystal doped with an activator impurity. In an embodiment the inorganic metal halide comprises an alkali metal halide. In an embodiment, the gamma ray scintillator means comprises inorganic crystals selected from one or more of: barium fluoride, bismuth germinate, cadmium tungstate, calcium fluoride doped with europium, calcium tungstate, caesium iodide, caesium iodide doped with sodium, caesium iodide doped with thallium, gadolinium oxysulfide, lanthanum bromide doped with cerium lanthanum chloride doped with cerium, lead tungstate, lutetium iodide, lutetium oxyorthosilicate, LYSO ($Lu_{1.8}Y_{0.2}SiO_5$(Ce), sodium iodide doped with thallium, yttrium aluminium garnet or zinc tungstate. In an embodiment the crystal comprises a micro-columnar crystal (e.g. with needle like crystals). In an embodiment the micro-columnar crystal is any one of a CsI, CsI(Na) or CsI(Tl) crystal. In an embodiment the gamma ray scintillator means comprises a scintillator detection plane to receive gamma-rays and wherein the relative position of the scintillator output flashes generated in the scintillator is preserved by the micro-columnar crystal as a collimated light output. In an embodiment the relative position of gamma rays incident on the scintillator detection plane is preserved in the relative position of the scintillator output flashes. In an embodiment the scintillator output flashes have a peak wavelength in the range 200 to 700 nm. In an embodiment the scintillator output flashes have a peak wavelength of 275 to 325, 375 to 425, or 525 to 575 nm. In an embodiment the scintillator converts gamma ray photons to visible photons with an efficiency of between 5 to 250 photons per keV, and optionally 25 to 75 photons per keV. In an embodiment the gamma ray scintillator means absorbs 5 to 70%, optionally 20 to 60%, and further optionally 30 to 50% of gamma rays incident on the scintillator detection plane. In an embodiment the gamma ray scintillator means is about 0.5 to 2.5 mm thick, optionally about 1 to 2 mm thick, and further optionally about 1.5 mm thick. In an embodiment the micro-columnar crystal is about 0.5 to 2.5 mm thick, optionally about 1 to 2 mm thick, and further optionally about 1.5 mm thick. In an embodiment the micro-columnar crystal is a CsI crystal and about 0.5 to 2.5 mm thick, optionally about 1 to 2 mm thick, and further optionally about 1.5 mm thick.

In an embodiment the gamma ray scintillator is a micro-columnar crystal, the micro-columnar crystal is a CsI crystal and this is 1.5 mm thick. Advantageously, a 1.5 mm thick CsI crystal provides efficient detection of gamma rays with good spatial resolution and at a reasonable cost. A large scintillator area improves resolution but results in a bigger device which is less favourable. A larger scintillator also requires an increased de-magnification of the tFOP in order to remain compatible with commercially available and affordable CMOS or CCD detectors, resulting in increased loss of light and therefore a reduction in sensitivity. In an embodiment the scintillator has a detection plane (to receive gamma-rays) surface area which is 10 to 10,000 $mm^2$, optionally 400 to 2,000 $mm^2$, and further optionally 700 to 1,400 $mm^2$. In an embodiment the diameter of a circular detection plane is 25-45 mm (~450-1,600 $mm^2$), optionally 30-40 mm (~700-1,300 $mm^2$), further optionally 33-37 mm (~800-1,100 $mm^2$), and still further optionally 34-36 mm (~900-1,200 $mm^2$) In an embodiment the scintillator has a detection plane (to receive gamma-rays) surface area which is more than 100, 250, 500, 1000, 10,000, 100,000 or 1,000,000 times greater than the surface area of the window. In an embodiment the scintillator has a detection plane (to receive gamma-rays) surface area which is more than 100, 250, 500, 1000, 10,000, 100,000 or 1,000,000 times greater than the surface area of the window, wherein the window is a pinhole. In an embodiment, the image projected from the pinhole covers between 90 to 110% of the scintillator surface area, optionally 93 to 97% of the scintillator surface area, further optionally 94 to 96% of the scintillator surface area. For example, if the input surface of the scintillator is circular and has a diameter of 35 mm (~960 $mm^2$), then when using a pinhole with a 60° cone angle, a spacing away from the sensor of 29.6 mm would give a projected image with a diameter of 34.2 mm (~920 $mm^2$ or corresponding to about 95% coverage of the scintillator surface area). Advantageously, this makes best use of the detection surface area of the scintillator without loss of light over the edge of the scintillator while avoiding use of the edge of the scintillator surface for imaging. So in the example above, to get between 90 and 100% coverage of the scintillator surface area, a distance of between 28.8 and 30.3 mm could be used. Using a sharper cone angle (e.g. 40-59°) would require a larger distance, increasing the size of the device, to get the same coverage of the same scintillator surface area. Using a broader cone angle (e.g. 61-90°) would require a smaller distance, which would reduce resolution of the device, to get the same coverage of the same scintillator surface area. Alternatively a larger scintillator surface area may be used, although this would also increase the size of the device and the cost of larger scintillators may be prohibitive. In an embodiment the cone angle and scintillator surface area are configured to achieve the optimum balance of device size, resolution, and cost. In an embodiment the pinhole has a cone angle of between 40-90°, optionally 50-70°, further optionally 55 to 65°, and still further optionally 60°. In an embodiment, where the cone angle is between 40-90° and the scintillator has a diameter between 25-45 mm, then a pinhole to scintillator distance may be in the range 15-45 mm, optionally 25-35 mm, further optionally 28-32 mm.

In an embodiment the first sensor means comprises a multiplication unit to concentrate and/or intensify the scintillator output flashes produced by the gamma ray scintillator means. Advantageously, this in effect greatly amplifies the signal from the gamma rays detected by the gamma ray scintillator.

In an embodiment the multiplication unit comprises a concentration means to concentrate the scintillator output flashes.

In an embodiment the multiplication unit comprises a concentration means to concentrate the scintillator output flashes, and wherein the concentration means comprises a lens or lens array.

In an embodiment the multiplication unit comprises a concentration means to concentrate the scintillator output flashes, and wherein the concentration means comprises a tapered fibre optic plate (tFOP) comprising an tFOP input surface to receive the scintillator output flashes and a tFOP output surface to output demagnified output flashes, wherein the surface area of the tFOP input surface is larger than the surface area of the tFOP output surface. Advantageously, the gamma rays detected by the scintillator output flashes are concentrated into a smaller surface area; this means that ultimately, a smaller sensor in the first signal digitisation means can be used. Such sensors, like complementary metal-oxide-semiconductor (CMOS) detectors or charge coupled devices (CCD), are expensive so minimizing their size is economically beneficial.

In an embodiment the temperature of the multiplication unit is controlled to minimise electronic noise that may degrade gamma ray source image quality. In an embodiment the multiplication unit is cooled. In an embodiment the temperature of the multiplication unit is controlled or cooled to below 35, 30 or 25° C.

In an embodiment the surface area of the scintillator is larger than the surface area of the sensor in the first signal digitisation means. In an embodiment the surface area of the scintillator is at least twice as large as the surface area of the sensor in the first signal digitisation means. In an embodiment the surface area of the scintillator is larger than the surface area of the detector. In an embodiment the surface area of the scintillator is at least twice as large as the surface area of the detector.

In an embodiment the surface area of the tFOP input surface is at least twice as large as the tFOP output surface. In an embodiment the surface area of the tFOP input surface to the tFOP output surface is in a ratio of between approximately 10:1 to approximately 1.1:1, optionally 5:1 to 1.5:1, further optionally it is approximately. 2:1 In an embodiment the surface area of the tFOP input surface to the tFOP output surface area is approximately 10:1, 8:1, 6:1, 4:1 or 2:1. In an embodiment the tFOP input surface should be greater than the tFOP output surface, but with the proviso that the ratio of the surface area of the tFOP input surface to the tFOP should not be greater than about 10:1, 8:1, 6:1, 4:1 or 2:1. It should be understood that as the size of the input surface increases relative to the output surface in the tapered FOP, light is lost, and the consequential gamma flashes can become hard to distinguish from the noise of the image intensifier. Accordingly, for example, a large input surface necessitates a correspondingly large tFOP output surface, and hence the resultant apparatus would not be portable and the cost of tFOP, image intensifier and CMOS or CCD detector would be prohibitive.

In an embodiment the relative position of the scintillator output flashes is preserved in the relative position of the demagnified output flashes. In an embodiment the relative position of gamma rays incident on the scintillator detection plane is preserved in the relative position of the demagnified output flashes. In an embodiment the tFOP comprises a core pitch in the range 0.5 to 100 μm, optionally 1 to 50 μm, and further optionally 3 to 20 μm. In an embodiment the tFOP input surface has a surface area equal or greater than 50, 100, 150, 160, 180, 200, 300, 500, 1000, 2000 or 5000 mm$^2$. In an embodiment the tFOP input surface has a surface area equal or less than 75, 100, 150, 160, 180, 200, 300, 500, 1000, 2000, 5000 or 10000 mm$^2$. In an embodiment the tFOP input surface is substantially circular, square or rectangular. In an embodiment the tFOP input surface is optically coupled with the gamma ray scintillator means. In an embodiment the tFOP input surface is in contact with the gamma ray scintillator means. In an embodiment the gamma ray scintillator means is grown/deposited on the tFOP input surface. In an embodiment, the surface area of the tFOP input surface substantially matches the scintillator detection plane surface area.

Herein disclosed, the concentration means is not part of the device according to the first aspect of the invention, and/or the embodiments thereof.

In an embodiment the multiplication unit comprises an electron output means to convert scintillator output flashes into output electrons. In an embodiment the electron output means comprises a photocathode. In an embodiment the photocathode has a quantum efficiency of 0.5 to 100%, optionally 5 to 50%, and further optionally 10 to 20%. In an embodiment the photocathode comprises a photocathode input surface to receive the demagnified output flashes and a photocathode output surface to output the output electrons. In an embodiment the relative position of the demagnified output flashes are preserved in the relative position of the output electrons. In an embodiment the relative position of gamma rays incident on the scintillator detection plane is preserved in the relative position of the output electrons. In an embodiment the photocathode input surface comprises an input FOP arranged to receive the scintillator output flashes. In an embodiment the photocathode input surface comprises an input FOP arranged to receive the concentrated scintillator output flashes. In an embodiment the photocathode input surface and input FOP are optically coupled. In an embodiment the photocathode input surface and input FOP are in contact. In an embodiment the gamma ray scintillator is deposited on the photocathode input surface. In an embodiment the photocathode input surface is a FOP or TFOP.

In an embodiment the electron output means comprises electron amplification means to amplify the number of output electrons and to generate an amplified electron output. In an embodiment the electron amplification means comprises a micro-channel plate. In an embodiment the electron amplification means comprises two or more micro-channel plates. In an embodiment the micro-channel plate comprises holes with a pitch of about 1 to 100 μm, optionally 5 to 50 μm, and further optionally 10 to 20 μm. In an embodiment the micro-channel plate has a micro-channel plate detection plane to receive output electrons and wherein the position of the output electrons incident on the micro-channel plate detection plane is preserved by the micro-channel plate as a collimated amplified electron output. In an embodiment the micro-channel plate comprises a micro-channel plate input surface to receive the output electrons and a micro-channel plate output surface to output the amplified electron output. In an embodiment the relative position of the output electrons is preserved in the relative position of the amplified electron output. In an embodiment the relative position of gamma rays incident on the scintillator detection plane is preserved in the relative position of the amplified electron output.

Herein disclosed, the electron output means is not part of the device according to the first aspect of the invention, and/or the embodiments thereof.

In an embodiment the multiplication unit comprises a phosphor means to convert the amplified electron output into phosphor output photons. In an embodiment the phosphor is selected such that the phosphor output photons are of a wavelength suitable for efficient detection by a CMOS or CCD detector. In an embodiment the phosphor output photons have a wavelength in the range 200 to 900 nm, optionally 300 to 800 nm, and further optionally 450 to 700 nm. In an embodiment the phosphor has a fluorescent lifetime compatible with the read rate of a CMOS or CCD detector such that spread of the phosphor flashes between detector frames are largely avoided. In an embodiment the phosphor has a fluorescent lifetime in the range 0.1 to 10 ms, optionally 0.5 to 5 ms, and further optionally 1 to 2 ms. In an embodiment the phosphor means has a phosphor detection plane to receive the amplified electron output and wherein the position of the amplified electron output incident on the phosphor detection plane is preserved. In an embodiment the phosphor means comprises a phosphor input surface to receive the amplified electron output and a phosphor output surface to output the phosphor output photons. In an embodiment the relative position of the amplified electron output is preserved in the relative position of the phosphor output photons. In an embodiment the relative position of gamma rays incident on the scintillator detection plane is preserved in the relative position of the phosphor output photons. In an embodiment the phosphor output surface comprises an output FOP arranged to output phosphor output photons. In an embodiment the phosphor output surface and output FOP are optically coupled. In an embodiment the phosphor output surface and output FOP are in contact.

Herein disclosed, the phosphor means is not part of the device according to the first aspect of the invention, and/or the embodiments thereof.

In an embodiment the electron output means and phosphor means together defined an intensification unit. In an embodiment the device comprises an intensification unit to intensify the scintillator output flashes produced by the gamma ray scintillator means. In an embodiment the multiplication unit comprises an intensification unit to intensify the scintillator output flashes produced by the gamma ray scintillator means. In an embodiment the intensified scintillator output flashes produced by the intensification unit are phosphor output photons. Advantageously, the scintillator output flashes are thereby intensified (e.g. more photons are produced and exit the intensification unit than originally entered it) and their spatial location relative to each other is preserved. In an embodiment the intensification unit comprises the input FOP arranged to receive scintillator output flashes, and the output FOP arranged to output phosphor output photons. In an embodiment the intensification unit is a modular unit. In an embodiment the intensification unit is a commercially available unit. In an embodiment the intensification unit may be used/replaced according to the need of the user. Advantageously, a modular unit, in particular a commercially available unit is a simple and convenient way to manufacture the device. As such, this offers an easy 'drop in' assembly design. This means the device is simpler to make.

Herein disclosed, the electron output means and phosphor means which together defined an intensification unit, is not part of the device according to the first aspect of the invention, and/or the embodiments thereof.

Herein disclosed, the scintillator is deposited on a tFOP or FOP and coupled directly to the CMOS or a CCD (e.g. an EMCCD). When deposited/directly coupled in this way, the interfaces between the layers are substantially eliminated. Advantageously, a tFOP gives better image resolution for a given size detector than a FOP. The tapered FOP (tFOP) contributes to better image quality, and lowers the cost of production, by increasing image resolution while still employing a small, standard size CMOS detector.

In an embodiment the tFOP input surface is optically coupled with the gamma ray scintillator means. In an embodiment the tFOP input surface is in contact with the gamma ray scintillator means. In an embodiment the tFOP output surface has substantially the same surface area as input surface of the amplification means. In an embodiment the gamma ray scintillator means is grown/deposited on the tFOP input surface. In an embodiment the tFOP output surface is optically coupled with the photocathode input surface. In an embodiment the tFOP output surface is in contact with the photocathode input surface. In an embodiment the tFOP output surface is optically coupled with the input FOP of the photocathode. In an embodiment the tFOP output surface is in contact with the input FOP of the photocathode. In an embodiment the tFOP comprises two or more separate plates. In an embodiment the input FOP of the photocathode comprises two or more separate plates. In an embodiment the separate plates are optically coupled. In an embodiment index matching optical grease or fluid is used in optically coupling of separate plates. In an embodiment the optical fibre sizes of the tFOP output surface and the micro-channel plate input surface, and/or the input FOP of the photocathode, are selected to minimise interference patterns. In an embodiment the scintillator is deposited on the tFOP input surface and the tFOP output surface is coupled directly to the CMOS or a CCD (e.g. an EMCCD) detector. In an embodiment the tFOP output surface has substantially the same surface area as input surface of the CMOS detector, although for example, a circular output may be projected onto a square input surface etc.

Advantageously, the tFOP gives better image resolution for a given size CMOS, and when deposited/directly coupled in this way, the interfaces between the layers are substantially eliminated; as such the associated interference problems caused by such interfaces are likewise substantially mitigated/eliminated.

Moire interference pattern effects are known in the art, and are interference patterns that can be produced when an opaque regular pattern with transparent gaps is overlaid on another similar pattern. In an embodiment the optical fibre sizes of the tFOP output surface and the micro-channel plate input surface, and/or the input FOP of the photocathode, are selected to minimise Moire interference pattern effects. In an embodiment the optical fibre sizes of the tFOP output surface and the plate/surface it is to be optically coupled with, or in contact with, are not in a ratio of approximately 1:1. In an embodiment the optical fibre sizes of the tFOP output surface and the plate/surface it is to be optically coupled with, or in contact with, are in a ratio of between approximately 10:1 to approximately 1:10. In an embodiment the ratio is approximately 2:1 or 1:2. In an embodiment the optical fibre sizes of the tFOP output surface and the micro-channel plate input surface, and/or the input FOP of the photocathode, are in a ratio of between approximately 10:1 to approximately 1:10. In an embodiment the ratio is approximately 2:1 or 1:2.

Advantageously, it has been found that non-matching patterns in the ratio ranges above, in particular the ratio of about 2:1, can reduce Moire interference pattern effects. Generally, as the ratio diverges from 2:1 or 1:2 the more significant the Moire interference pattern effects become.

In an embodiment the optical fibre sizes of the tFOP output surface are approximately 1 to 50 μm, optionally 2 to 30 μm, and further optionally approximately 10 μm. In an embodiment the optical fibre sizes of the micro-channel plate input surface, and/or the input FOP of the photocathode, are approximately 1 to 50 μm, optionally 2 to 20 μm, and further optionally approximately 5 μm. In an embodiment the optical fibre sizes of the tFOP output surface are approximately 10 μm, and the fibre sizes of the plate/surface it is to be optically coupled with, or in contact with, are approximately 5 μm. This ratio of about 2:1 has been found to be particularly effective at reducing Moire interference pattern effects. In an embodiment the optical fibre sizes of the tFOP output surface are approximately 10 μm and the micro-channel plate input surface, and/or the input FOP of the photocathode, are approximately 5 μm. In an embodiment the tFOP, input FOP of the photocathode, photocathode and/or micro-channel plate are arranged to prevent movement relative to each other.

In an embodiment the first sensor means comprises first signal digitisation means to convert scintillator output flashes, or intensified scintillator output flashes into first signals for use in forming a first image of the subject. In an embodiment the first sensor means comprises first signal digitisation means to convert phosphor output photons into first signals for use in forming a first image of the subject. Advantageously, it is useful to digitise the phosphor output photons. This allows for storage, manipulation and transmission of the image data as needed. The digitised signals can be processed on-board the device or they can be transmitted to a further device for processing or further processing. For example, filters and data conditioning processes can be applied to the data as necessary to improve the final image produced.

In an embodiment the first signal digitisation means comprises a complementary metal-oxide-semiconductor (CMOS) detector or charge coupled device (CCD) or electron multiplying CCD (EMCCD). In an embodiment the first signal digitisation means comprises a CMOS or sCMOS detector. In an embodiment the CMOS detector is responsive to the phosphor output photons. In an embodiment the CMOS detector comprises CMOS digitisation means arranged to receive and convert CMOS output electrons into first signals for use in forming a first image of the subject. Advantageously a CMOS sensor is faster, lower cost and has lower read noise than an equivalent CCD/EMCCD sensor. It was found that the CMOS detector did not require significant cooling, obviating the need for a pressure vacuum (to eliminate traces of moisture that would condense on the cooled surface of an EMCCD and cause degradation of the detector).

In an embodiment the multiplication unit comprises a fibre optic plate conduit (FOPc) to transport phosphor output photons from the phosphor means to the first signal digitisation means. In an embodiment the multiplication unit comprises a FOPc to transport phosphor output photons from the phosphor means to the CMOS detector. In an embodiment the FOPc is the output FOP of the phosphor output surface. In an embodiment the FOPc is optically coupled to the FOP of the phosphor output surface. In an embodiment the FOPc is in contact with the FOP of the phosphor output surface. In an embodiment the FOPc comprises a FOPc input surface to receive the phosphor output photons and a FOPc output surface to output the transported phosphor output photons. In an embodiment the relative position of the phosphor output photons is preserved in the relative position of the transported phosphor output photons.

In an embodiment the relative position of gamma rays incident on the scintillator detection plane is preserved in the relative position of the transported phosphor output photons. In an embodiment the FOPc input surface is optically coupled with the phosphor means. In an embodiment the FOPc input surface is in contact with the phosphor means. In an embodiment the FOPc output surface is optically coupled with the CMOS detector. In an embodiment the FOPc output surface is in contact with the CMOS detector. In an embodiment the FOPc comprises two or more separate plates. In an embodiment the separate plates are optically coupled. In an embodiment the separate plates are substantially parallel. In an embodiment all separate plates are substantially parallel. In an embodiment the separate plates are optically coupled to minimise interference patterns. In an embodiment all separate plates are optically coupled to minimise interference patterns. In an embodiment the separate plates are optically coupled to minimise Moire interference patterns. In an embodiment all separate plates are optically coupled to minimise Moire interference patterns. In an embodiment the optical fibre sizes of a first FOPc output surface and a second FOPc input surface are in a ratio of between approximately 10:1 to approximately 1:10. In an embodiment the ratio is 2:1 or 1:2. In an embodiment the optical fibre sizes of a first FOPc output surface are approximately 1 to 50 μm, optionally 5 to 30 μm, and further optionally approximately 4 μm. In an embodiment the optical fibre sizes of a second FOPc input surface are approximately 1 to 50 μm, optionally 5 to 30 μm, and further optionally approximately 8 μm. In an embodiment the optical fibre sizes of a first tFOP output surface are approximately 10 μm and the optical fibre sizes of a second FOPc input surface are approximately 8 μm. In an embodiment the first FOPc and second FOPc plates are arranged to prevent movement relative to each other. In an embodiment index matching optical grease or fluid is used to couple the separate plates of the FOPc.

In an embodiment the gamma ray scintillator means is located between the window and concentration means. In an embodiment the concentration means is located between the gamma ray scintillator means and electron output means. In an embodiment the electron output means is located between the concentration means and electron amplification means. In an embodiment the electron amplification means is located between the electron output means and the phosphor means. In an embodiment the phosphor means is located between the electron amplification means and the first signal digitisation means. In an embodiment the FOPc is located between the phosphor means and the first signal digitisation means.

In an embodiment the device comprises control means for controlling the first sensor means and second sensor means to simultaneously generate respective first signals and second signals in response to concurrent gamma and light rays from the subject. In an embodiment the device comprises signal processing means arranged to receive first signals and to generate first image data from the first signals representing an image of the subject according to gamma rays; and to receive second signals and to generate second image data from the second signals representing an image of the subject according to light rays. In an embodiment the device comprises signal processing means arranged to receive first signals and second signals and to generate composite image data from the first signals and second signals representing an image composite of both the image of the subject according to gamma rays and concurrently according to light rays. In an embodiment the device is arranged such that the signal output from the CMOS can be deconvolved to enhance the gamma image resolution. In an embodiment the device comprises signal output means arranged to transmit the composite image data and/or the first image data and/or second image data; optionally this is transmitted wirelessly. In an embodiment the signal processing means is arranged to transmit the first image data and/or second image data at a frame rate that substantially avoids buffering of the data and delay in reconstruction and display of the resultant images. Advantageously, the device is equipped with on-board control means to effectively work the device. The control means may for example fully or partially process any signal data such that downstream processing is reduced or substantially eliminated. Processing may use one or more filters or data conditioning processes. Reducing downstream processing can improve real-time display of the images captured by the first and second sensors. Concurrently processing to provide first signals and second signals of the image data captured by the first and second sensors may therefore be processed and displayed as first and second images in real-time, or near real-time. The resultant first and second images may also be combined, in effect overlaid, to generate a composite image, and transmitted as a composite image signal.

In an embodiment the device is mains powered or battery powered. Advantageously, the device requires low power and so a single cable can be used to provide power and to transmit data. In an embodiment the device is powered via a power-over-ethernet (PoE) cable. In that way, a single (POE) cable can be used for device control, data transfer from two signal channels and as the power supply means. Alternatively, due to low power use, a battery may provide sufficient power for extended use. In an embodiment the battery is rechargeable. In an embodiment the device is plug-and-play. In an embodiment the device comprises all the electronics necessary to operate the device. In an embodiment the device comprises a display means to display image data or operational data. In an embodiment the device is arranged to connect directly or wirelessly to a smart phone, tablet, processor or computer; or application/program hosted thereon. In an embodiment the device is arranged for duel isotope imaging. In an embodiment the device is arranged for single isotope imaging. In an embodiment the device is arranged for imaging gamma photons with energy of 35 to 750 KeV. In an embodiment the device is arranged for imaging of Tc-99m, I-123, I-131, Lu-177, In-111, Y-90, Sc-47, Ga-67, Cr-51, Sn-177m, Cu-67, Tm-167, Ru-97, Re-188, Au-199, Pb-203, Ce-141, Co-57, F-18, Ga-68, C-11, O-15, N-13, Zr-89, Rb-82, Cu-64.

In an embodiment the device is operable at room temperature and pressure. In an embodiment the device can be operated continuously at room temperature and pressure throughout a working day without degradation of image quality. In an embodiment, in use the device does not comprise a region at a temperature equal or below 10, 5, 0, −5, or −10° C. In an embodiment the device does not comprise a region that requires cooling to a temperature equal or below 10° C. In an embodiment the device does not comprise a phase changing material used to provide cooling. In an embodiment the device does not comprise a region under vacuum. In an embodiment the device does not comprise a region that is destructively sensitive to atmospheric humidity.

In an embodiment the device is small. In an embodiment the device is portable. In an embodiment the device has a mass equal or less than 5, 4, 3, 2, or 1 kg. In an embodiment the device has a mass equal or greater than 4.5, 4, 3, 2, 1, or 0.5 kg. In an embodiment the device has a mass of between 2 and 3 kgs. In an embodiment the device has a volume equal or less than 5, 4, 3, 2.5, 2, 1.5, 1, 0.5, 0.25 litres. In an embodiment the device has a volume equal or greater than 4.5, 4, 3, 2.5, 2, 1.5, 1, 0.5, 0.1 litres. In an embodiment the device is ergonomic, and optionally is substantially cylindrical. Advantageously, the device may be small and portable. For example, it may be easily held in one hand and can be carried easily by one person. In use, it may be prudent to use two hands or the device may be supported by a stand. This means that the device can be taken to where it is needed, for example direct to patients. For example, the device can be taken to an elderly person who has poor mobility, or taken to a clinic or even to a person's home.

In an embodiment the device comprises a light source for use in illuminating the subject, optionally the light source comprises LEDS. In an embodiment the light source gives off visible, UV or IR light, optionally the light causes fluorescence in the subject being illuminated. In an embodiment the light source has a wavelength that is suitable for use in fluorescence imaging. In an embodiment the LEDs form a perimeter around the subject-facing portion of the device. In an embodiment the device comprises a distance sensor to measure and/or record the distance between the device and the subject. In an embodiment the device comprises a motion sensor to correct for subject movement during image acquisition. In an embodiment the gamma ray scintillator means is not directly in contact with a charge-coupled device (CCD) or CMOS. In an embodiment the device has a quantum efficiency equal or greater than 5, 10, 20, 30, 40, 50, 60, 70, 80, 90%.

In a second aspect of the invention, there is provided a system comprising one or more devices according to the first aspect of the invention, and together with one or more of a: display; display monitor, support stand/frame, movable arm, power supply, battery, memory, Wi-Fi capability, Bluetooth capability, communication interface, and communication cables.

In an embodiment the system comprises one or more devices arranged to generate a 3D image. In an embodiment the system is portable. Advantageously, the device of the first aspect of the invention may be combined into a larger system so as to provide convenient use of the device. This may include ways to transmit image data out of the device and ways to relay information/instructions to the device. The system may include dedicated display devices like display monitors. The system may include external data processing units or memory units. The system may include extra and/or external cooling means to remove heat from the device. The system may be supported on a frame, the frame may be equipped with wheels to aid in movement. The frame may have a moveable arm to support and position the device.

In a third aspect of the invention, there is provided a use of the device or system according to the first or second aspect of the invention to image a subject using gamma rays and light rays emanating from the subject.

In an embodiment the subject is imaged using only the gamma rays emanating from the subject. In an embodiment the first image from the first sensor means and second image from the second sensor means are superimposed. In an embodiment an imaging agent is administered to the subject prior to imaging the subject. In an embodiment the imaging agent is a fluorescent agent. In an embodiment the fluorescent agent is selected from one or more of a reactive and conjugated dye, Nucleic acid dye, Cell function dye or Fluorescent protein. In an embodiment the fluorescent agent is selected from one or more of Hydroxycoumarin, Aminocoumarin, Methoxycoumarin, Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, G-Dye100, G-Dye200, G-Dye300, G-Dye400, Cyt, Cy3, Cy3B, Cy3.5, Cy5, Cy5.5, Cy7, TRITC, X-Rhodamine, Lissamine Rhodamine B, Texas Red, Allophycocyanin (APC), APC-Cy7 conjugates, Hoechst 33342, DAPI, Hoechst 33258, SYTOX Blue, Chromomycin A3, Mithramycin, YOYO-1, Ethidium Bromide, Acridine Orange, SYTOX Green, TOTO-1, TO-PRO-1, TO-PRO: Cyanine Monomer, Thiazole Orange, CyTRAK Orange, Propidium Iodide (PI), LDS 751, 7-AAD, SYTOX Orange, TOTO-3, TO-PRO-3, DRAQS, DRAQ7, Dye, Indo-1, Fluo-3, Fluo-4, DCFH, DHR, SNARF, GFP (Y66H mutation), GFP (Y66F mutation), EBFP, EBFP2, Azurite, GFPuy, T-Sapphire, Cerulean, mCFP, mTurquoise2, ECFP, CyPet, GFP (Y66 W mutation), mKeima-Red, TagCFP, AmCyan1, mTFP1, GFP (S65A mutation), Midoriishi Cyan, Wild Type GFP, GFP (S65C mutation), TurboGFP, TagGFP, GFP (S65L mutation), Emerald, GFP (S65T mutation), EGFP, Azami Green, ZsGreenl, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("REP"), mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, or mRaspberry.

In an embodiment the imaging agent is a gamma ray emitting agent. In an embodiment the gamma ray emitting agent comprises one or more radioisotopes. In an embodiment the gamma ray emitting agent is selected from one or more of Tc-99m, I-123, I-131, Lu-177, In-111, Y-90, Sc-47, Ga-67, Cr-51, Sn-177m, Cu-67, Tm-167, Ru-97, Re-188, Au-199, Pb-203, Ce-141, Co-57. In an embodiment the gamma ray emitting agent accumulates in cells, tissue and/or an organ to be imaged. In an embodiment the fluorescent agent accumulates in cells, tissue and/or an organ to be imaged. In an embodiment the cells, tissue and/or organ to be imaged is selected from one or more of: bladder, bone, blood, blood vessel, brain, colon, eye, gall bladder, heart, intestine, kidney, liver, lung, pancreas, skin, stomach, thyroid or parathyroid. In an embodiment the cells, tissue and/or an organ to be imaged comprises abnormal cell growth. In an embodiment the cells, tissue and/or an organ to be imaged comprise cancer. In an embodiment the cells, tissue and/or an organ is imaged performing one or more biological functions. In an embodiment the biological function comprises a physical function. In an embodiment the physical function comprises filling, emptying, contracting or relaxing. In an embodiment the physical function is imaged in real-time.

Herein disclosed is a method of using the device of the first or second aspect to image a subject using gamma rays emanating from the subject.

In a fourth aspect of the invention, there is provided a method of imaging a subject using a device or system according to the first or second aspect of the invention, the method comprising:

permitting both gamma rays and light rays emanating from the subject to be communicated to the separation means, the separation means arranged to separate the gamma rays and light rays emanating from the subject into a gamma ray channel comprising gamma rays and a light ray channel comprising light rays;

the first sensor means is arranged to receive and detect the gamma rays from the gamma ray channel and to generate first signals for use in forming a first image of the subject;

the second sensor means is arranged to receive and detect the light rays from the light ray channel and to generate second signals for use in forming a second image of the subject;

forming a first image of the subject from the first signals;

forming a second image of the subject from the second signals; and displaying the first image and second image.

In an embodiment the first image and second image are displayed individually, adjacent or are superimposed. In an embodiment the first image and second image are fully or partially overlaid. In an embodiment the first image and second image are superimposed.

Herein disclosed is a method of analysis or diagnosis comprising the step of imaging a subject using the device or system according to the first or second aspect of the invention.

In an embodiment the device or system is portable and is brought to the subject to be imaged.

Herein disclosed is a method of treatment or surgery comprising the step of imaging a subject during the treatment or surgery using the device or system according to the first or second aspect of the invention.

In an embodiment the subject is treated with a gamma ray emitting agent which accumulates in tissue to be removed in the surgery, optionally the tissue comprises cancer.

Herein disclosed is a method of evaluating a treatment or surgery conducted on a subject, comprising the step of imaging the subject after the treatment or surgery using the device or system according to the first or second aspect of the invention.

In an embodiment the subject is human or animal or part or tissue thereof; or the subject may be non-human or non-animal and contain or be contaminated with a gamma ray emitting substance. In an embodiment the device or system is portable and is brought to the subject to be imaged.

In an embodiment the subject is human or animal or part or tissue thereof; or the subject may be non-human or non-animal and contain or be contaminated with a gamma ray emitting substance. In an embodiment the device or system is portable and is brought to the object/subject to be imaged.

Herein disclosed, the disclosure herein above, inclusive of the aspects and/or embodiments of the invention may be adapted/used for non-medical imaging, e.g. for imaging inanimate subject objects using both suitable gamma rays and light rays emanating from the subject, optionally having utility in radioactive waste management, identifying small localised leaks involving radioactivity, or in radiation protection. For example, suitable applications may include: finding/detecting/monitoring accidental spills of gamma ray emitting components (e.g. a spilled component used in a medical treatment, or a spilled component used in a laboratory); finding/detecting/monitoring/localising the possible inadvertent removal of gamma-ray emitting components from a store; finding/detecting/monitoring/localising spent/waste low grade gamma-ray emitting components used in connection with industry; finding/detecting/monitoring/localising possible inadvertent radioactive contamination; or monitoring the integrity of containment vessels holding/storing gamma emitting components used in connection with industry.

Embodiments or disclosures disclosed herein may be independently combined with any other embodiment, embodiments, aspect or aspects of the invention.

The present invention will now be further described with reference to the following non-limiting examples and the accompanying illustrative drawings, of which:

BRIEF DESCRIPTION OF THE DRAWINGS

Like features have been given like reference numerals.

DETAILED DESCRIPTION OF THE INVENTION

Figure 1:
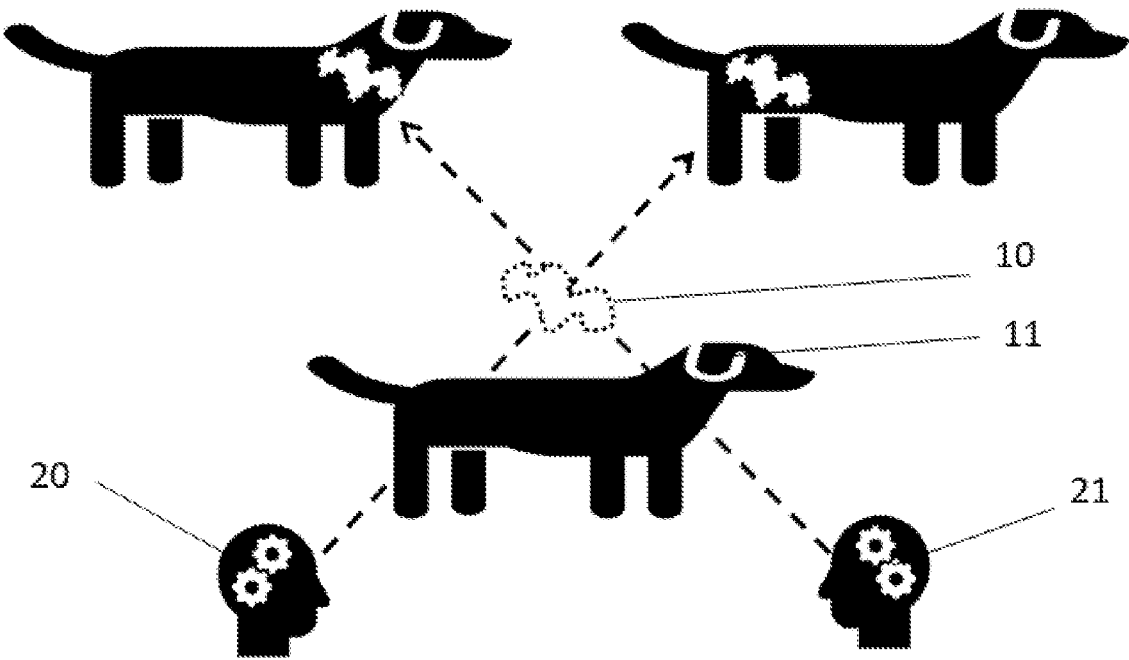
FIG. 1 is a schematic representation of the phenomena of parallax.

FIG. 1 is a schematic representation of the phenomena of parallax. A radioactive object (10) is located behind a subject (11) and is observed by the left observer (20) and the right observer (21). The observers are capable of visualising the radioactive object and the subject. Due to parallax, the left observer (20) will observe the object (10) towards the rear of the subject (11), whereas the right observer (21) will observe the object (10) towards the front of the subject (11). Indeed, the situation is even more complex than this representation provides for. This is because the 'observers' are (i) optical and (ii) gamma, so the images are different in appearance and there are no common features in the images that can be used to align or reference to, even when using image analysis algorithms.

Figure 2:
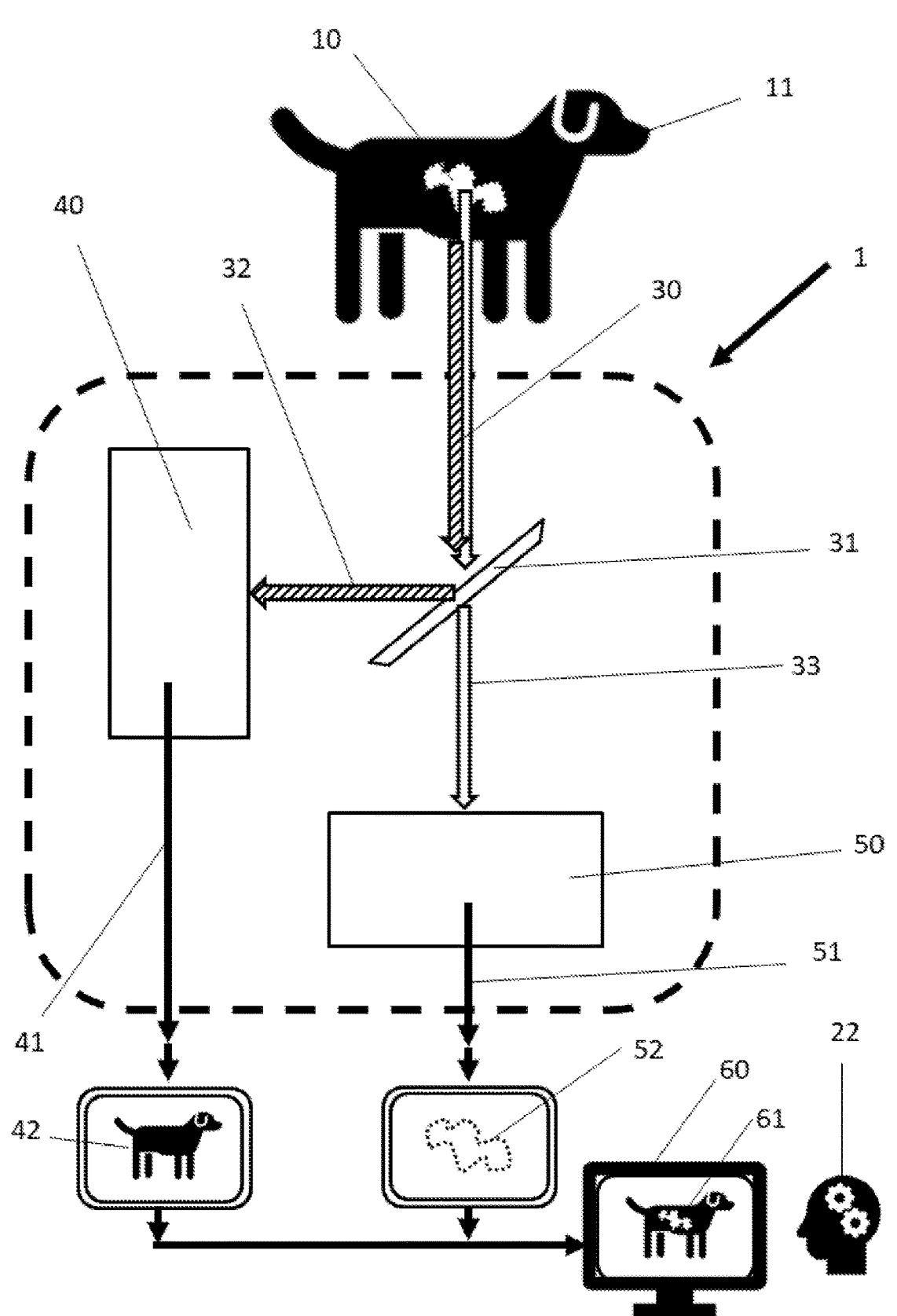
FIG. 2 is a schematic representation of an embodiment of the invention.

FIG. 2 is a schematic representation of an embodiment of the invention (1). A subject (11) contains a gamma ray emitting substance (10). Gamma rays and light rays together (30) travel from the subject (11) on substantially coincidental paths and enter the device and hit the separation means (31), which is in the form of a mirror angle at 45 degrees to the line of travel of the rays.

The light rays reflect off the mirror (31) producing a light ray channel (32), the light ray channel (32) travels towards and is detected by the second sensor means (40). The second sensor means (40) generates second signals (41) which are transmitted from the device and are use in forming a second image (42) of the subject (11). The second image is an image of a dog.

The gamma rays pass through the mirror (31) producing a gamma ray channel (33), the gamma ray channel (33) travels towards and is detected by the first sensor means (50). The first sensor means (50) generates first signals (51) which are transmitted from the device and are use in forming a first image (52) of the subject. The first image (52) is an image of the gamma ray emitting substance.

The first (52) and second (42) images are superimposed and displayed as a composite image (61) on a display monitor (60). The composite image (61) is an image showing the location of the gamma ray emitting substance within the dog. The composite image (61) is observed by an observer (22).

Figure 3:
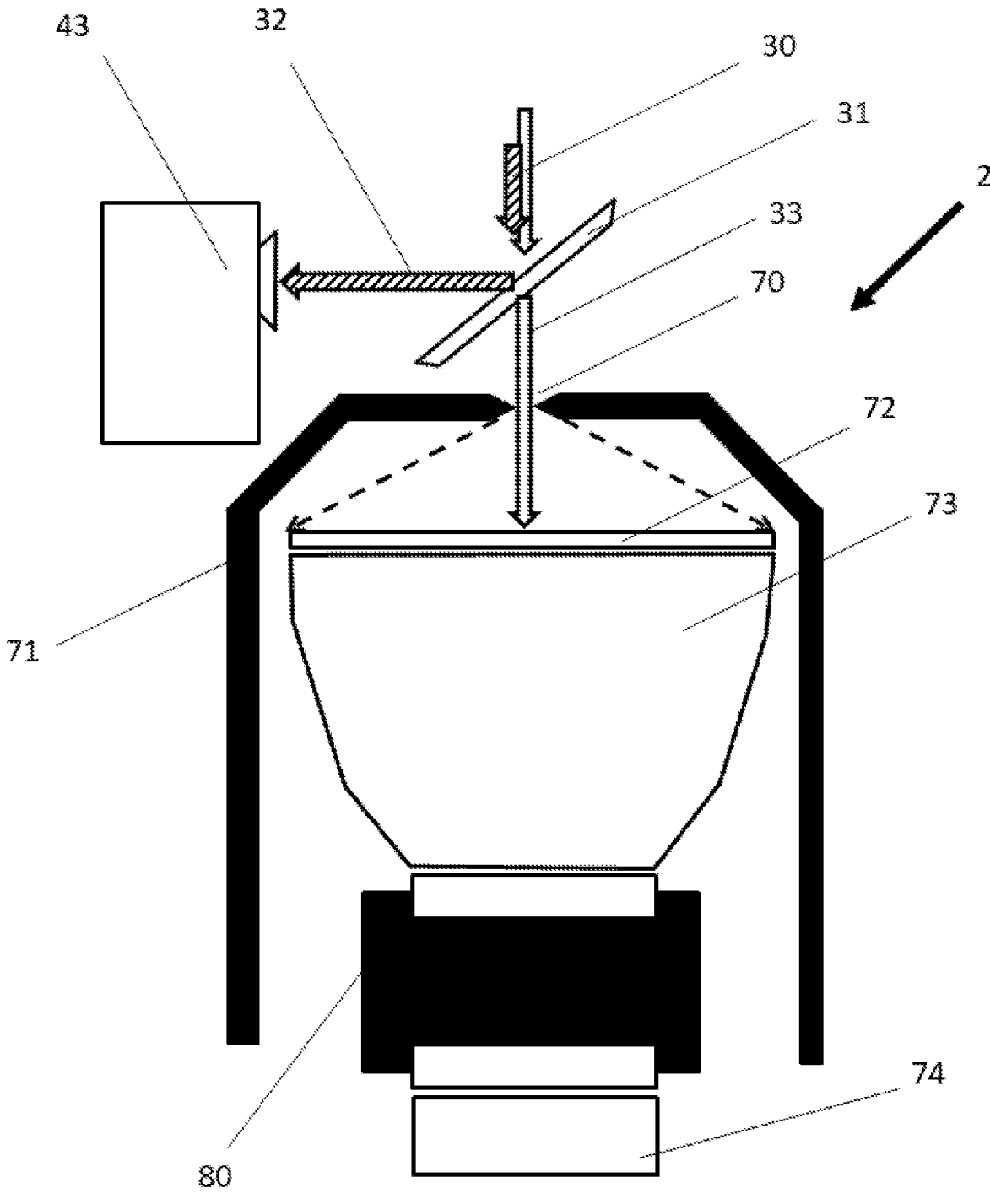
FIG. 3 is a schematic cross sectional representation of an embodiment of the invention.

FIG. 3 is a schematic cross sectional representation of an embodiment of the invention (2).

A subject (not shown) contains a gamma ray emitting substance. Gamma rays and light rays together (30) travel from the subject on substantially coincidental paths (30) and enter the device and hit the separation means (31), which is in the form of a mirror angle at 45 degrees to the line of travel of the rays.

The light rays reflect off the mirror (31) producing a light ray channel (32), the light ray channel (32) travels towards and is detected by the second sensor means in the form of a digital camera (43). The second sensor means (43) generates second signals (not shown).

The gamma rays pass through the mirror (31) producing a gamma ray channel (33), the gamma ray channel (33) passes through a pinhole collimator (70) in the tapered tungsten chamber (71) and is detected by a gamma ray scintillator means in the form of a photocathode. The dashed lines indicate the permitted angle which gamma rays may enter and strike the gamma ray scintillator means (72). The gamma ray scintillator means (72) is grown on a tapered fibre optic plate tFOP (73). The tFOP demagnifies the scintillator flashes (not shown) generated by the gamma ray scintillator means (72). The commercially available intensification unit (80) receives the demagnified scintillator flashes and produces phosphor output photons (not shown). The phosphor output photons are detected and converted into first signals (not shown) by a first signal digitisation means (74).

Figure 4:
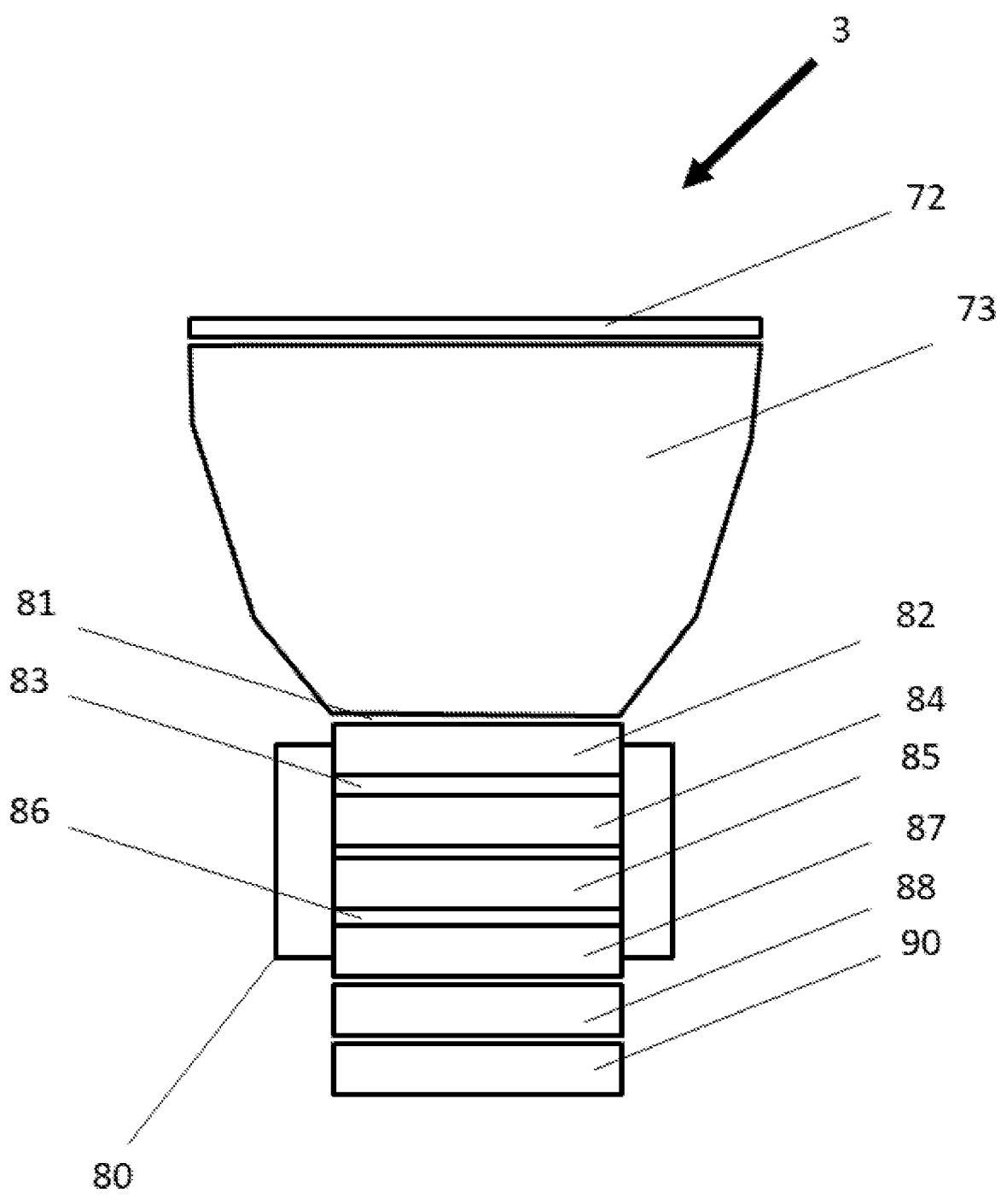
FIG. 4 is a schematic cross sectional representation part of an embodiment of the invention.

FIG. 4 is a schematic cross sectional representation of part of an embodiment (3) of the invention shown in FIG. 3.

The gamma ray scintillator means in the form of a CsI(Tl) crystal (72) is grown on a tapered fibre optic plate tFOP (73). The tFOP is adjacent to the intensification unit (80) and is optically coupled by optical grease to the input FOP (82) of the intensification unit (80).

The intensification unit (80) is made of several layers: an input FOP (82) to receive the demagnified scintillator photons; which is adjacent to a photocathode (83) to receive the demagnified scintillator photons from the input FOP (82) and to produce output electrons; which is adjacent to the first micro-channel plate (84); which is adjacent to the second micro-channel plate (85), both of which amplify the number of electrons; which is adjacent to a phosphor unit (86), which receives the electrons from the second micro-channel plate (85), and produces phosphor output photons; and which is adjacent to the output FOP (87), the output FOP (87) transmitting the phosphor output photons out of the intensification unit (80).

The output FOP (87) is optically coupled by optical grease to a CMOS detector (90), which converts the received phosphor output photons into first signals (not shown) via a fibre optic coupler (88).

Figure 5:
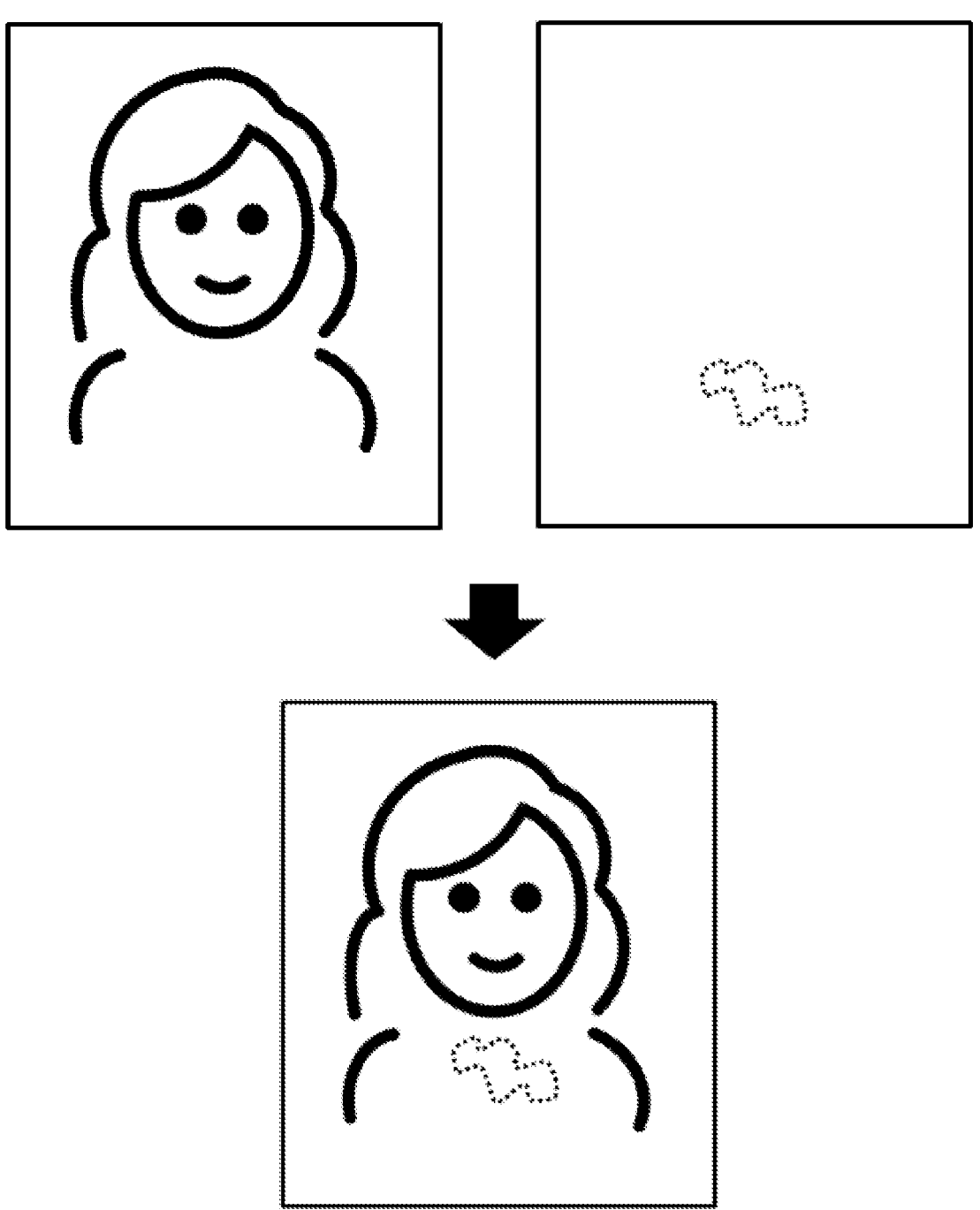
FIG. 5 shows schematically gamma and optical ray images and the same images superimposed.

FIG. 5 shows schematically gamma and optical ray images and the same images superimposed. The left image of a person is captured by the second sensor (optical) means of an embodiment of the invention. The right image shows the same object but captured with the first sensor (gamma) means of the invention. The bottom image is a superimposed composite image of the left and right image and so shows the spatial location of the gamma ray emitting object. The composite image is useful in identifying the zone where the radio isotope has accumulated.

Figure 6:
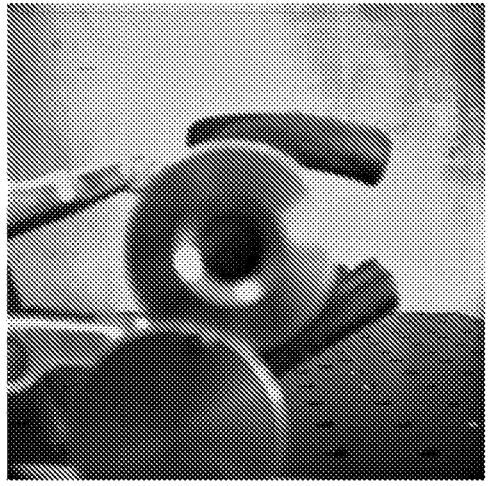
FIG. 6 shows gamma and optical ray images, and the same images superimposed.
Figure 6:
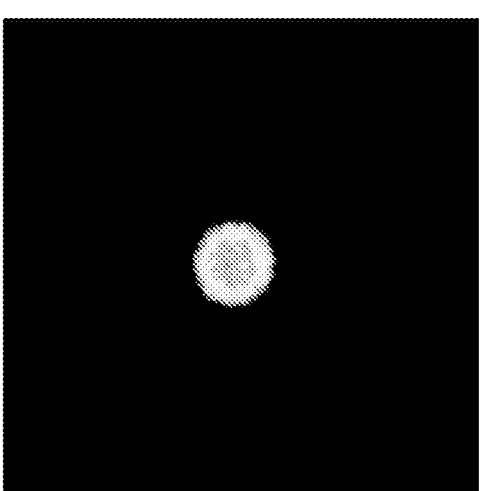
Figure 6:
Figure 6:
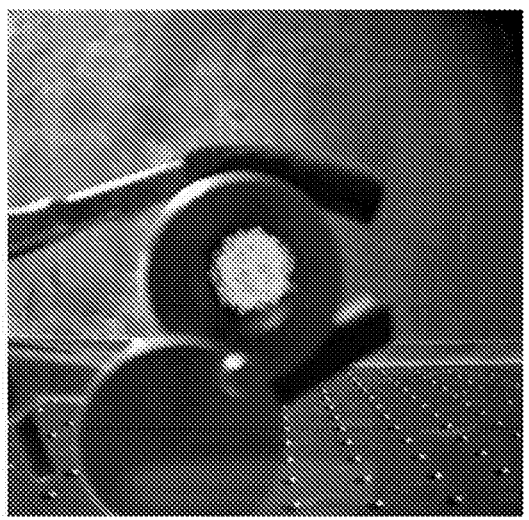

FIG. 6 shows, like FIG. 5, gamma and optical ray images and the same images superimposed. The left image shows the feed from a second sensor (optical) means of an embodiment of the invention. The right image shows the same object but captured with the first sensor (gamma) means of the invention. The bright central spot shows the accumulated counts of gamma photons originating from the radioactive source. The bottom image is a superimposed composite image of the left and right image and so shows the spatial location of the gamma ray emitting object. The composite image is useful in identifying the zone where the radio isotope is located.

Figure 7:
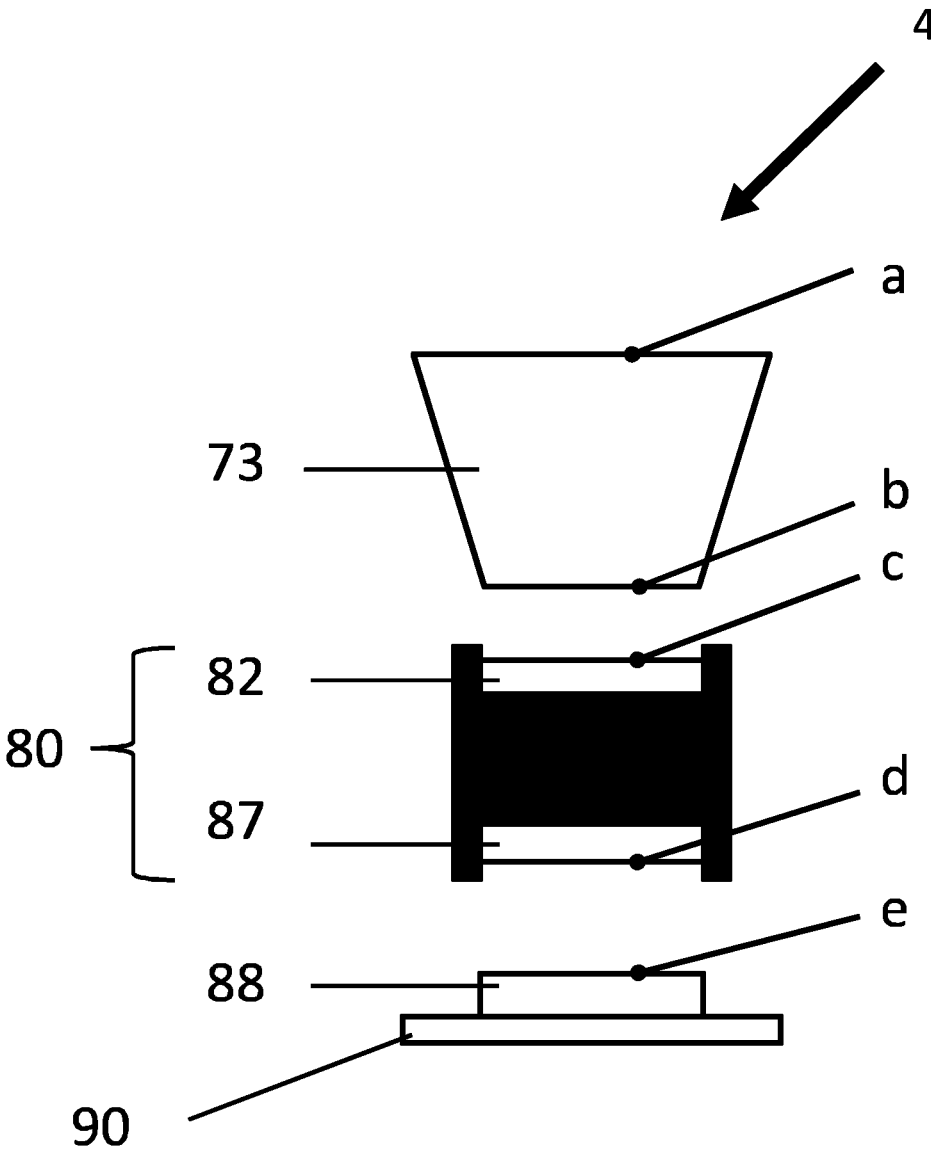
FIG. 7 shows a schematic section of fibre optic elements of an embodiment of the invention.

FIG. 7 is a schematic cross sectional representation of the fibre optic elements in the optic chain of an embodiment (4) of the invention shown in FIG. 7. The reference numerals (73, 80, 82, 87, 88, 90) correspond to those shown in FIGS. 3 and 4. In an embodiment, the pitch of the fibres in the fibre optic elements are (a)=14 µm, (b)=7 µm, (c)=5.5 µm, (d)=4.2 µm, and (e)<6 µm. In another embodiment, the pitch of the fibres in the fibre optic elements are (a)=20 µm, (b)=10 µm, (c)=5.5 µm, (d)=4.2 µm, and (e)=8 µm. Different pitches are considered, inclusive of pitches between these two embodiments, e.g. the pitch of fibres at (a) may be between 14 and 20 µm. Also considered are the same relative ratios between adjacent zones; e.g. the ratio between pitch size (a):(b) is 2:1, and/or the ratio of (d):(e) is 1:2.

The invention claimed is:

1. A medical imaging device for use in imaging a subject using both gamma rays and light rays emanating from the subject, the device comprising:

separation means to separate gamma rays and light rays emanating from the subject into a gamma ray channel comprising gamma rays and a light ray channel comprising light rays;

first sensor means arranged to receive and detect gamma rays from the gamma ray channel and to generate first signals for use in forming a first image of the subject;

second sensor means arranged to receive and detect light rays from the light ray channel and to generate second signals for use in forming a second image of the subject;

wherein the first sensor means and the second sensor means are arranged to receive gamma rays and light rays, respectively, which propagate from the subject upon substantially coincident paths.

2. The device according to claim 1, wherein the separation means comprises a mirror arranged at substantially 45 degrees to gamma and light rays propagating from the subject.

3. The device according to claim 1, wherein the first sensor means is housed in a chamber substantially opaque to gamma rays, the chamber comprising a window arranged to receive gamma rays from the gamma ray channel, and wherein the window is substantially transparent to gamma rays.

4. The device according to claim 3, wherein the chamber comprises a tapered end, the tapered end tapering towards the window.

5. The device according to claim 3, wherein the window comprises, or is comprised of, a pinhole.

6. The device according to claim 3, wherein the chamber comprises a movable member comprising two or more movable windows of different sizes and/or shapes, wherein the movable member is reversibly movable such that at least one of the movable windows of different size and/or shape is arranged to form the window in the chamber.

7. The device according to claim 1, wherein the first sensor means comprises a gamma ray scintillator means responsive to gamma rays and which produces scintillator output flashes of light in response to incidences of gamma rays.

8. The device according to claim 7, wherein the gamma ray scintillator is deposited on the surface of a Fibre Optic Plate (FOP).

9. The device according to claim 8 wherein the Fibre Optic Plate (FOP) is a tapered Fibre Optic Plate (tFOP).

10. The device according to claim 9 wherein the optical fibre sizes of the tFOP output surface and the plate/surface it is to be optically coupled with, or in contact with, are in a ratio of approximately between approximately 10:1 to approximately 1:10.

11. The device according to claim 10 wherein the ratio is approximately 2:1 or 1:2.

12. The device according to claim 7, wherein the first sensor means comprises first signal digitisation means to convert scintillator output flashes, or intensified scintillator output flashes, into first signals for use in forming a first image of the subject.

13. The device according to claim 12, wherein the first signal digitisation means comprises a complementary metal-oxide-semiconductor (CMOS) detector or charge coupled device (CCD).

14. The device according to claim 1, wherein the first sensor means comprises a multiplication unit to concentrate and/or intensify the scintillator output flashes produced by the gamma ray scintillator means.

15. The device according to claim 14, wherein the multiplication unit comprises a concentration means to concentrate the scintillator output flashes, and wherein the concentration means comprises a tapered fibre optic plate (tFOP) comprising an tFOP input surface to receive the scintillator output flashes and a tFOP output surface to output demagnified output flashes, wherein the surface area of the tFOP input surface is larger than the surface area of the tFOP output surface.

16. The device according to claim 14, wherein the multiplication unit comprises an intensification unit to intensify the scintillator output flashes produced by the gamma ray scintillator means.

17. The device according to claim 1, wherein device is powered via a power-over-ethernet (PoE) cable.

18. A system comprising one or more devices according to claim 1, and together with one or more of a: display; display monitor, support stand/frame, movable arm, power supply, battery, memory, Wi-Fi capability, Bluetooth capability, communication interface, and communication cables.

19. A method of imaging a subject using a device according to claim 1, the method comprising:

permitting both gamma rays and light rays emanating from the subject to be communicated to the separation means, the separation means arranged to separate the gamma rays and light rays emanating from the subject into a light ray channel comprising light rays and a gamma ray channel comprising gamma rays;

the first sensor means is arranged to receive and detect the gamma rays from the gamma ray channel and to generate first signals for use in forming a first image of the subject;

the second sensor means is arranged to receive and detect the light rays from the light ray channel and to generate second signals for use in forming a second image of the subject;

forming a first image of the subject from the first signals;

forming a second image of the subject from the second signals; and displaying the first image and second image.

\* \* \* \* \*